US012792867B2

(12) United States Patent
Leibbrand et al.

(10) Patent No.: US 12,792,867 B2
(45) **Date of Patent: *Nov. 10, 2026**

(54) RADIO FREQUENCY IDENTIFICATION (RFID) INLAYS FOR USE WITH MEDICAL INJECTION DEVICES

(71) Applicants: Becton, Dickinson and Company, Franklin Lakes, NJ (US); Becton Dickinson France, Le Pont-de-Claix (FR)

(72) Inventors: Alfred Leibbrand, Claix (FR); Nicolas Euvrard, London (GB); Cédric Rivier, Voreppe (FR); Gwenn Le Dimet, Charavines (FR); Damien Maréchal, Claix (FR); Thierry Vasquez, Vaulnaveys-le-Haut (FR)

(73) Assignees: Becton, Dickinson and Company, Franklin Lakes, NJ (US); Becton Dickinson France, Le Pont-de-Claix (FR)

( * ) Notice: Subject to any disclaimer, the term of this patent is extended or adjusted under 35 U.S.C. 154(b) by 0 days.

This patent is subject to a terminal disclaimer.

(21) Appl. No.: 19/310,106

(22) Filed: Aug. 26, 2025

(65) Prior Publication Data

US 2026/0030474 A1 Jan. 29, 2026

Related U.S. Application Data

(63) Continuation of application No. 18/781,206, filed on Jul. 23, 2024, now Pat. No. 12,423,547, which is a (Continued)

(51) Int. Cl.
*G06K 19/07* (2006.01)
*A61M 39/20* (2006.01)

(Continued)

(52) U.S. Cl.
CPC ......... *G06K 19/0723* (2013.01); *A61M 39/20* (2013.01); *G09F 3/0295* (2013.01)

(58) Field of Classification Search
CPC .............. G06K 19/0723; G09F 3/0295; G09F 2003/0272

(Continued)

(56) References Cited

U.S. PATENT DOCUMENTS 8,695,819 B1 4/2014 Anderson
9,311,592 B1 4/2016 Vitello et al.

(Continued)

FOREIGN PATENT DOCUMENTS

DE 102019108253 A1 10/2020
EP 4152300 A1 3/2023

(Continued)

*Primary Examiner* — Toan C Ly
(74) *Attorney, Agent, or Firm* — The Webb Law Firm

(57) ABSTRACT

A tip cap assembly for coupling with a syringe body includes a luer lock adaptor, a rigid cap coupled to the luer lock adaptor; a rigid tip cap having distal end and proximal ends, the rigid tip cap being disposed at least partially within the rigid cap, a RFID tag positioned over the distal end of the tip cap, and an adhesive layer formed over the RFID tag. Also provided is RFID inlay for use with medical devices including a meshed substrate, and a RFID antenna and integrated circuit assembly adhered to the meshed substrate. A syringe and label assembly is disclosed, including a body having distal and proximal ends, a tip cap assembly having distal end and proximal ends, and a label at least partially surrounding the distal end of the syringe body and the proximal end of the tip cap, the label comprises an integrated RFID tag.

20 Claims, 8 Drawing Sheets

Related U.S. Application Data continuation of application No. 17/922,101, filed as application No. PCT/US2021/057531 on Nov. 1, 2021, now Pat. No. 12,067,438.

(60) Provisional application No. 63/124,126, filed on Dec. 11, 2020, provisional application No. 63/108,497, filed on Nov. 2, 2020.

(51) Int. Cl.
*G09F 3/00* (2006.01)
*G09F 3/02* (2006.01)

(58) Field of Classification Search
USPC .......................................................... 235/492
See application file for complete search history.

(56) References Cited

U.S. PATENT DOCUMENTS

| | | | |
|---|---|---|---|
| 10,035,624 | B2 | 7/2018 | Bauss |
| 10,661,935 | B2 | 5/2020 | McKinnon et al. |
| 2002/0188259 | A1 | 12/2002 | Hickle et al. |
| 2005/0023173 | A1 | 2/2005 | Paoletti |
| 2008/0306443 | A1 | 12/2008 | Neer et al. |
| 2015/0090625 | A1 | 4/2015 | Bauss |
| 2020/0164161 | A1 | 5/2020 | Murray et al. |
| 2020/0268480 | A1 | 8/2020 | Bauss et al. |
| 2021/0236736 | A1 | 8/2021 | Murray et al. |
| 2022/0180143 | A1 | 6/2022 | Rehm |
| 2022/0257872 | A1 | 8/2022 | Geissler et al. |
| 2023/0023532 | A1 | 1/2023 | Oetzel et al. |

FOREIGN PATENT DOCUMENTS

| | | | |
|---|---|---|---|
| JP | 200242096 | A | 2/2002 |
| JP | 200871071 | A | 3/2008 |
| JP | 2008150903 | A | 7/2008 |
| JP | 201969393 | A | 5/2019 |
| WO | 2009104362 | A1 | 8/2009 |
| WO | 2019189449 | A1 | 10/2019 |
| WO | 2019189451 | A1 | 10/2019 |
| WO | 2020194644 | A1 | 10/2020 |
| WO | 2020219482 | A1 | 10/2020 |
| WO | 2021001291 | A1 | 1/2021 |
| WO | 2022094382 | A1 | 5/2022 |

RADIO FREQUENCY IDENTIFICATION (RFID) INLAYS FOR USE WITH MEDICAL INJECTION DEVICES

CROSS-REFERENCE TO RELATED APPLICATIONS

This application is a continuation of U.S. patent application Ser. No. 18/781,206 filed Jul. 23, 2024, which is a continuation of U.S. patent application Ser. No. 17/922,101 filed Nov. 1, 2021 (now U.S. Pat. No. 12,067,438), which is the United States national phase of International Application No. PCT/US2021/057531 filed Nov. 1, 2021, and claims priority to U.S. Provisional Application Ser. No. 63/108,497, filed Nov. 2, 2020, entitled "Radio Frequency Identification (RFID) Inlays for Use with Medical Injection Devices", and 63/124,126, filed Dec. 11, 2020, entitled "Radio Frequency Identification (RFID) Inlays for Use with Medical Injection Devices", the entire disclosures of each of which are hereby incorporated by reference in their entirety.

BACKGROUND

Field of the Disclosure

The present disclosure relates to medical injection devices utilizing data tags or inlays, such as radio frequency identification (RFID) tags or inlays, including methods of manufacturing such devices.

Description of the Related Art

Medical injection devices such as, e.g., pre-fillable or prefilled syringes usually include a hollow body or barrel forming a container for a medical product. This body includes a distal end which optionally may be provided with a needle, and a proximal end, usually provided with a flange.

There is an increasing need for individual traceability of medical containers such as medical injection devices, with such traceability extending from the manufacturing process until the final labeling, final use, and/or disposal of the medical containers.

While it has been known to utilize machine-readable identifiers such as bar codes, QR codes, and/or RFID tags in order to provide traceability of products such as, e.g., medical injection devices, such identifiers are often accessible from the surface of the containers or other devices, making the identifiers potentially subject to damage or tampering. Additionally, the location of many existing identifiers on the devices is often not conducive to effective and efficient scanning/reading.

SUMMARY

In view of the foregoing, there exists a need for a traceable identifiers such as RFID tags or inlays which may be resistant to damage and/or tampering, provide further evidence in the event of tampering, and/or provide for improved machine readability. There is also a need for tracking a medical device from the manufacturing steps to the disposal step of said medical device. There is also a need for providing a medical evidence having a tamper evidence function.

Embodiments of the present disclosure are directed to a tip cap assembly for coupling with a medical device such as a vial or a syringe, typically a pre-filled syringe. The tip cap assembly is configured to be coupled to a syringe body, the tip cap assembly including a luer lock adaptor, a rigid cap coupled to the luer lock adaptor, and a rigid tip cap having a distal end and a proximal end, the rigid tip cap being disposed at least partially within the rigid cap. The tip cap assembly further includes a RFID tag positioned over the distal end of the rigid tip cap. An adhesive layer may be formed over the RFID tag. The tip cap assembly may be coupled to a syringe via a luer lock adaptor which is threaded to a distal tip of the syringe body.

In some embodiments, the RFID tag is formed as a circular RFID inlay.

In some embodiments, the RFID tag extends across the entire distal end of the rigid tip cap.

In some embodiments, the RFID tag is one of an ultra-high frequency (UHF) RFID tag, a high frequency (HF) RFID tag, a high frequency-near-field communication (HF-NFC) RFID tag, or a low frequency (LF) RFID tag.

In some embodiments, the adhesive layer is one of a UV-cured adhesive, a rubber adhesive, a wet inlay, a silicone adhesive, or a resin.

Further embodiments of the present disclosure are directed to a RFID inlay for use with medical devices. The RFID inlay includes a meshed substrate and a RFID antenna and integrated circuit chip assembly adhered to the meshed substrate.

In some embodiments, the meshed substrate is porous and gas permeable.

In some embodiments, the meshed substrate is formed of high-density spunbound polyethylene fibers.

Further embodiments of the present disclosure are directed to a syringe and label assembly. The syringe and label assembly includes a syringe body having a distal end and a proximal end, as well as a tip cap assembly having a distal end and a proximal end. The syringe and label assembly further includes a label at least partially surrounding the distal end of the syringe body and the proximal end of the tip cap, wherein the label comprises an integrated RFID tag.

In some embodiments, the label is formed of a tubular, heat-shrinkable material.

In some embodiments, the tip cap assembly is a rigid needle shield.

In some embodiments, the tip cap assembly comprises a rigid outer shield made of plastic material and a flexible inner shield made of rubber material.

In some embodiments, the rubber inner shield is disposed at least partially within the plastic rigid shield.

In some embodiments, the label further comprises a tear-off etching line.

In some embodiments, the tear-off etching line passes through a portion of the integrated RFID tag.

Further embodiments of the present disclosure are directed to a label for use with syringe and tip cap assemblies. The label includes a tubular body, a RFID tag adhered to, or formed as part of, the tubular body, and a tear-off etching line configured to break the tubular body.

In some embodiments, the tubular body is formed of a heat-shrinkable material.

In some embodiments, the tear-off etching line passes through a portion of the RFID tag.

Further embodiments of the present disclosure are directed to a tip cap assembly for coupling with a syringe body including a luer lock adaptor, a rigid cap coupled to the luer lock adaptor, and a rigid tip cap having a distal end and a proximal end, the rigid tip cap being disposed at least partially within the rigid cap. The tip cap assembly further includes a RFID tag positioned within the rigid cap and over the distal end of the rigid tip cap.

In some embodiments, the RFID tag is formed as a circular RFID inlay.

In some embodiments, the RFID tag is retained within the rigid cap by an adhesive.

In some embodiments, the adhesive is applied to an outer circumferential edge of the RFID inlay.

Further embodiments of the present disclosure are directed to a tip cap assembly for coupling with a syringe body including a luer lock adaptor, wherein the luer lock adaptor comprises at least one annular groove, a rigid cap coupled to the luer lock adaptor, and a rigid tip cap, wherein the rigid tip cap is disposed at least partially within the rigid cap. The tip cap assembly further includes a RFID tag positioned within the at least one annular groove of the luer lock adaptor.

In some embodiments, the at least one annular groove is positioned at a distal end portion of the luer lock adaptor.

In some embodiments, the RFID tag is over-molded into the at least one annular groove.

In some embodiments, the RFID tag is clipped into the at least one annular groove.

In some embodiments, the RFID tag is ring-shaped.

Further embodiments of the present disclosure are directed to a tip cap assembly for coupling with a syringe body including a luer lock adaptor, a rigid cap coupled to the luer lock adaptor, and a rigid tip cap, wherein the rigid tip cap is disposed at least partially within the rigid cap. The tip cap assembly further comprises a RFID tag positioned around at least a portion of the luer lock adaptor.

Further embodiment of the present disclosure are directed to a tip cap assembly for coupling with a syringe body including a luer lock adaptor, a rigid cap coupled to the luer lock adaptor, and a rigid tip cap, wherein the rigid tip cap is disposed at least partially within the rigid cap. The tip cap assembly further includes a RFID tag positioned around at least a distal portion of the luer lock adaptor and a proximal portion of the rigid cap.

In some embodiments, the RFID tag further comprises a tear-off etching line.

In some embodiments, the tear-off etching line is positioned at a parting location between the distal portion of the luer lock adaptor and the proximal portion of the rigid cap.

Further details and advantages of the present disclosure will be understood from the following detailed description read in conjunction with the accompanying drawings.

DESCRIPTION OF THE INVENTION

Figure 1:
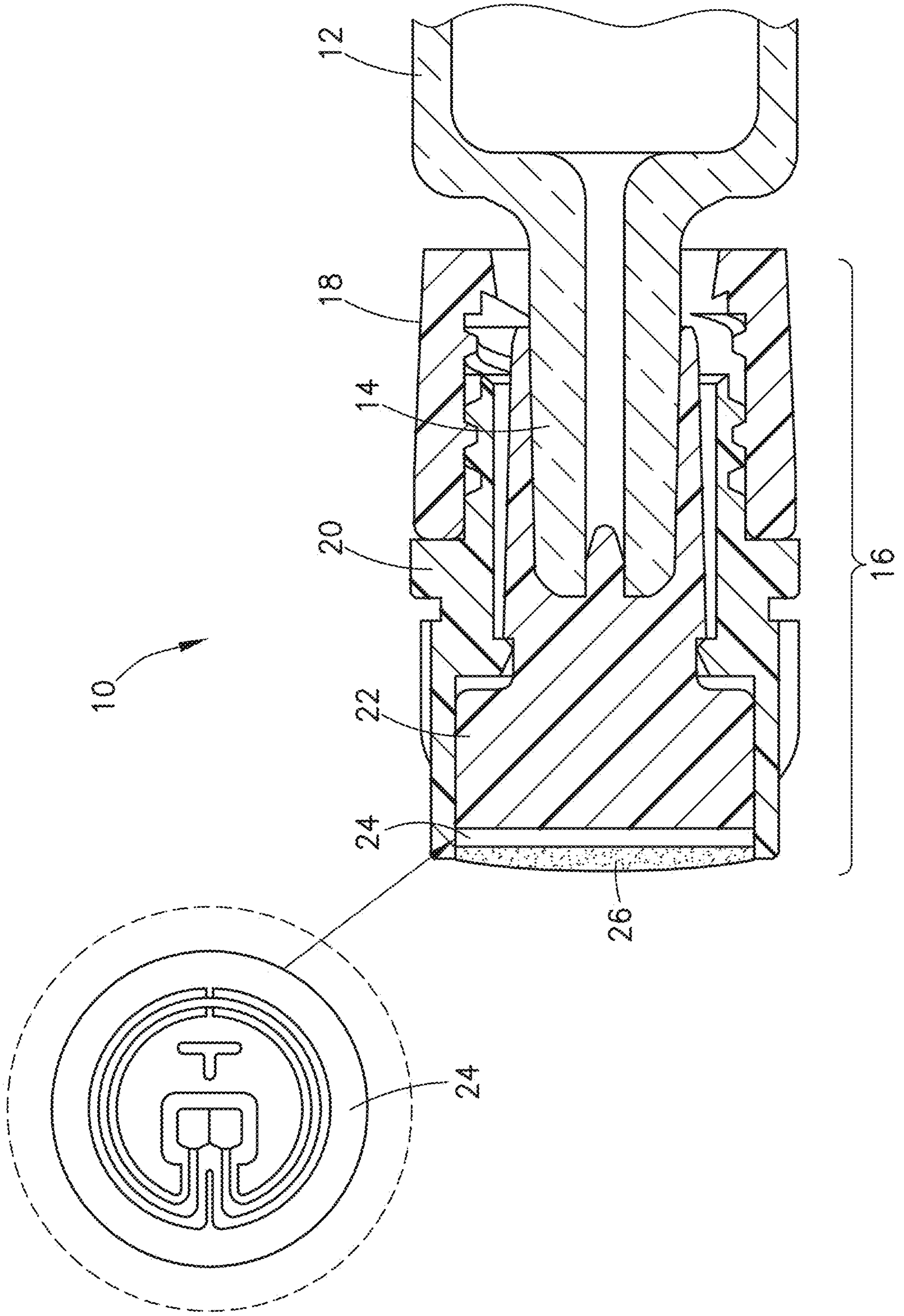
FIG. 1 is a partial cross-sectional side view of a syringe body and tip cap assembly incorporating a RFID inlay in accordance with an aspect of the present disclosure.

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Figure 2:
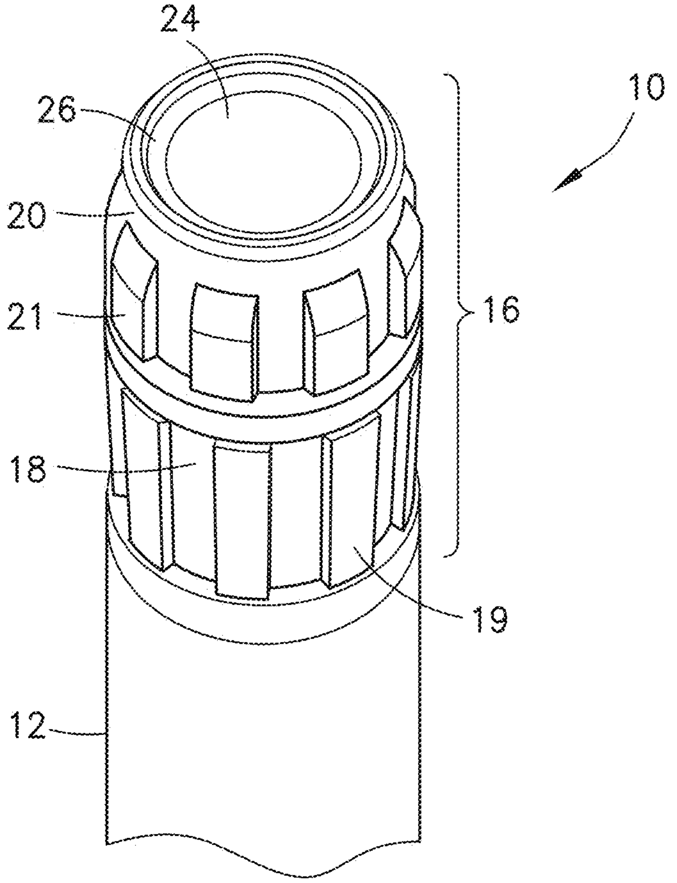
FIG. 2 is an isometric view of the syringe body and tip cap assembly incorporating a RFID inlay of FIG. 1.
Figure 3:
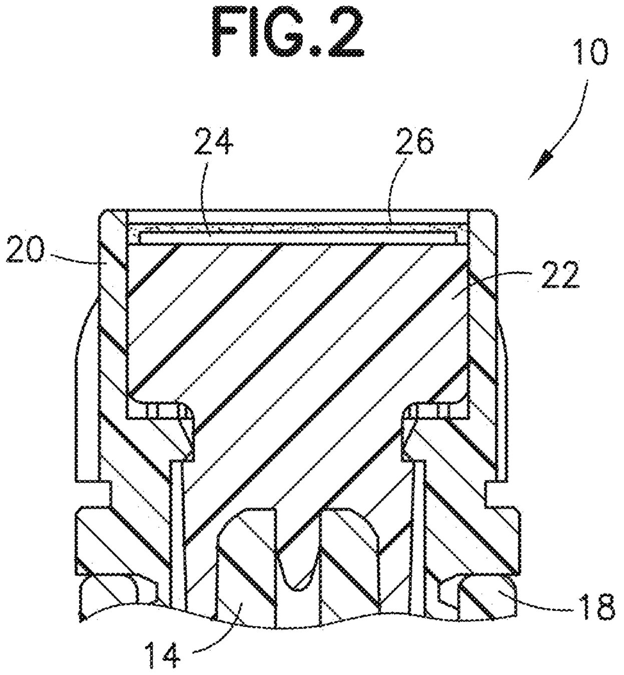
FIG. 3 is another partial cross-sectional side view of the syringe body and tip cap assembly incorporating a RFID inlay of FIG. 1.

Referring to FIGS. 1-3, various views of a syringe body and tip cap assembly 10 in accordance with an aspect of the present disclosure is shown. The syringe body and tip cap assembly 10 includes a syringe body 12 having a tip portion 14, as well as a plastic rigid tip cap (PRTC) assembly 16. The plastic rigid tip cap assembly 16 may be formed of multiple pieces, including a luer lock adaptor 18, a rigid cap 20, and a rigid tip cap 22 disposed within the rigid cap 20 and configured to at least partially surround the tip portion 14 of syringe body 12. The luer lock adaptor 18 may also be independent from the tip cap assembly 10. Typically, the rigid tip cap 22 is made of rubber material or typical material known from the skilled person enabling the sterilization gas to pass through the distal end of said rigid tip cap 22. Preferably, the rigid cap 20 is made of plastic material.

As is shown in FIG. 2, the luer lock adaptor 18 may include a plurality of ribs 19, while the rigid cap 20 may also include a plurality of ribs 21. The respective ribs 19, 21 may provide for enhanced grip by an assembly tool and/or a user's hand when attaching and/or removing the rigid cap 20, the luer lock adaptor 18, or both.

Additionally, at a distal end of the plastic rigid tip cap assembly 16, a RFID tag 24 may be provided. In some embodiments, RFID tag 24 is formed as a substantially circular RFID inlay. However, it is to be understood that the RFID tag 24 is not limited to a substantially circular inlay form, and may be any appropriate RFID tag. The RFID tag 24 may formed as, e.g., an ultra-high frequency (UHF) RFID tag, a high frequency (HF) RFID tag, a high frequency-near-field communication (HF-NFC) RFID tag, and/or a low frequency (LF) RFID tag. Additionally and/or alternative, the antenna of RFID tag 24 may be a dipole, or may be made of one or several loops. Furthermore, while RFID tag 24 is shown and described herein, it is to be understood that other forms of remotely writable and readable data tags and/or inlays may be utilized in accordance with the present disclosure. For example, data tags or inlays such as Bluetooth tags, an ultra-wide-band real-time location system (RTLS), a WiFi RTLS, and/or an infrared RTLS may be utilized in lieu of (or in addition to) a RFID tag.

As shown in FIGS. 1-3, the RFID tag 24 may be applied to a circular distal end of the plastic rigid tip cap assembly 16 and held or retained in position at that end by way of an adhesive 26. Adhesive 26 may be formed of any appropriate adhesive such as, e.g., a UV-cured adhesive, a rubber adhesive, a glue, a wet inlay, a silicon adhesive, a resin (e.g., an epoxy), etc. As is shown in FIG. 2, the adhesive 26 may be disposed as an annular bead around the outer circumferential edge of the RFID tag 24, thereby adhering the RFID tag 24 to at least the rigid cap 20. In other embodiments, the adhesive 26 may be formed as a layer disposed some or all of the RFID tag 24. In this way, not only does adhesive 26 retain RFID tag 24 within the distal end of the plastic rigid tip cap assembly 16, but it also acts to form a protective layer over RFID tag 24, thereby reducing the likelihood of damage or tampering.

In some embodiments, the RFID tag 24 may be sized to extend across substantially the entire surface of the distal end of the plastic rigid tip cap assembly 16, thereby maximizing antenna length and, thus, reading range. However, in other embodiments, it is to be understood that RFID tag 24 may be sized so as to only partially extend across the distal end of the plastic rigid tip cap assembly 16. In some embodiments, the RFID tag 24 may be configured to be disposed on an external and distal surface of the rigid cap 20. Furthermore, the rigid cap 20 may be formed in a rubber material.

To manufacture the plastic rigid tip cap assembly 16 having a RFID tag 24, the rigid cap 20 and a rigid tip cap 22 may first be provided and assembled together via, e.g., a snap-fit connection. Then, the assembled rigid cap 20 and rigid tip cap 22 may be coupled to the luer lock adaptor 18 via, e.g., a threaded connection. The coupling to the luer lock may also occur once the luer lock adaptor 18 is fixed to the distal tip 14 of the syringe via, e.g., snap-fitting or gluing. Next, the RFID tag 24 may be positioned over the distal end of the rigid tip cap 22, and the adhesive 26 may be formed about or over the RFID tag 24 so as to retain the RFID tag 24 over the rigid tip cap 22 relative to the rigid cap 20.

In the embodiment shown in FIGS. 1-3, the RFID tag 24 is maintained in the XY plane relative to the syringe body 12 and the plastic rigid tip cap assembly 16. With such an orientation, reading distance of the RFID tag 24 may be maximized. Additionally, this orientation enables the RFID tag 24 to be more easily read from the bottom of a tub of medical injection devices, as a plurality of the medical injection devices are generally held within the tub in an upright orientation.

Another advantage of the configuration shown in FIGS. 1-3 is that many suppliers utilize plastic rigid tip cap assemblies similar to those shown, allowing the construction of such a device to be subcontracted. Furthermore, a circular RFID inlay such as that which is shown may be less expensive than other RFID technologies (such as, e.g., solid RFID tags). Also, because the RFID tag 24 is simply added to plastic rigid tip cap assembly 16 and held by way of, e.g., adhesive 26, there is no impact or changes necessary to the molding of the components of the plastic rigid tip cap assembly 16 and/or the syringe 12.

Figure 4:
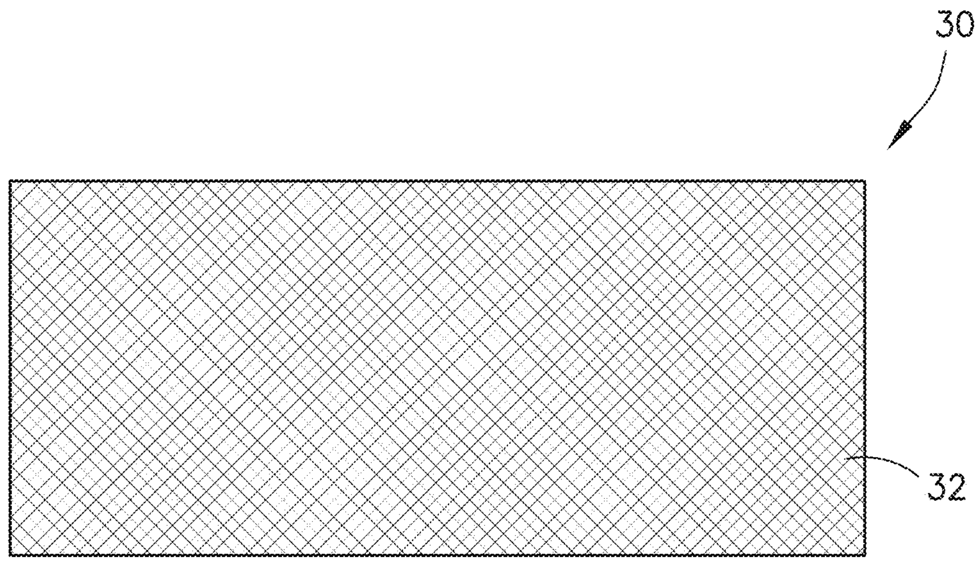
FIG. 4 is a top view of a meshed substrate for a label in accordance with an aspect of the present disclosure.
Figure 5:
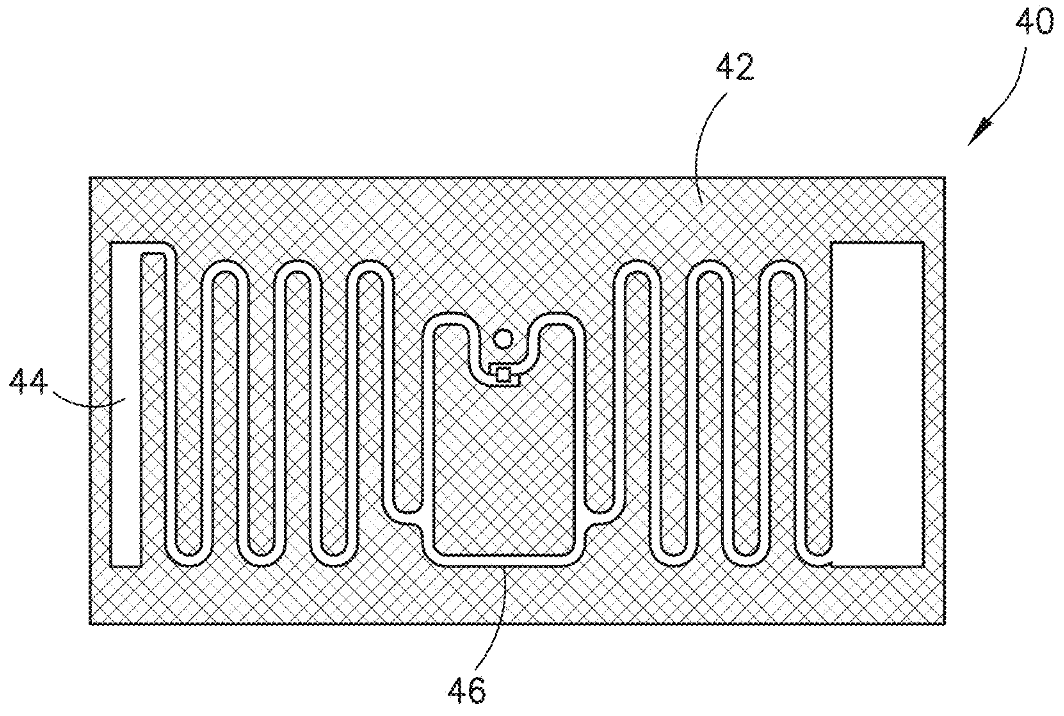
FIG. 5 is a top view of a meshed substrate for a RFID inlay in accordance with an aspect of the present disclosure.

Next, referring to FIGS. 4 and 5, a meshed substrate for use with labels and/or RFID inlay in accordance with other aspects of the disclosure are shown.

Most conventional labels used with medical devices such as, e.g., medical injection devices, utilize a solid film formed of, e.g., polyethylene terephthalate (PET), polyimide (PI), or paper. However, such labels are generally not porous and are applied after the device has been formed, thereby limiting their transparency to gasses used for sterilization and/or limiting their adhesion to the device. Furthermore, such solid film labels may trap gasses and/or humidity.

Conversely, FIG. 4 illustrates a label 30 having a meshed substrate 32 in accordance with an aspect of the present disclosure. The meshed substrate 32 may be formed of a thin mesh material such as, e.g. a pierced, porous layer of PET, PI, or paper. Examples of such a material include, e.g., Tyvek®, Gore-Tex® films, bandage material, etc.

By utilizing a label 30 having a meshed substrate 32, an adhesive such as a UV cure or resin (e.g., polypropylene) may penetrate the meshed substrate 32 during processing, thereby enabling attachment of the label 30 to various device parts during processes such as, e.g., in-mold labeling, gluing, in-molding, etc. Furthermore, the meshed substrate 32 enables gases to penetrate therethrough, allowing for, e.g., sterilization (EtO, steam, etc.), degassing, desorption, exudation, etc. The meshed substrate 32 also prevents the capture of gasses or humidity in the label 30.

In order to manufacture the label 30, one or more layers of a porous substrate material such as, e.g., Tyvek® may be used, along with an adhesive in the event that more than one layer is present. Alternatively, a solid film material (or layers of solid film material) may be initially utilized, with small holes or micro-perforations puncturing the material spread across the entire surface to form the meshed substrate 32.

Referring to FIG. 5, a RFID inlay 40 utilizing a similar meshed substrate is shown. Specifically, RFID inlay 40 includes a meshed substrate 42, along with a RFID antenna 44 and integrated circuit (IC) chip 46.

As with meshed substrate 32 described above, the meshed substrate 42 may be formed of a thin mesh material such as, e.g. a pierced, porous layer of PET, PI, or paper. Examples of such a material include, e.g., Tyvek®, Gore-Tex® films, bandage material, etc.

By utilizing the meshed substrate 42, an adhesive such as a UV cure or resin (e.g., polypropylene) may penetrate the RFID inlay 40 during processing, thereby enabling attachment of the RFID inlay 40 to various device parts during processes such as, e.g., in-mold labeling, gluing, in-molding, etc. Furthermore, the meshed substrate 42 enables gases to penetrate therethrough, allowing for, e.g., sterilization (EtO, steam, etc.), degassing, desorption, exudation, etc. The meshed substrate 42 also prevents the capture of gasses or humidity in the RFID inlay 40.

In order to manufacture the RFID inlay 40, one or more layers of a porous substrate material (i.e., a high-density spunbound polyethylene fiber such as, e.g., Tyvek®) may be used, along with an adhesive in the event that more than one layer is present. Additionally, the RFID antenna 44 and IC chip 46 may be printed/assembled and adhered to the meshed substrate 42. Alternatively, a solid film material (or layers of solid film material) may be initially utilized, with small holes or micro-perforations puncturing the material spread across the entire surface to form the meshed substrate 42, with the RFID antenna 44 and IC chip 46 then printed/assembled and adhered to the meshed substrate 42.

Figure 6A:
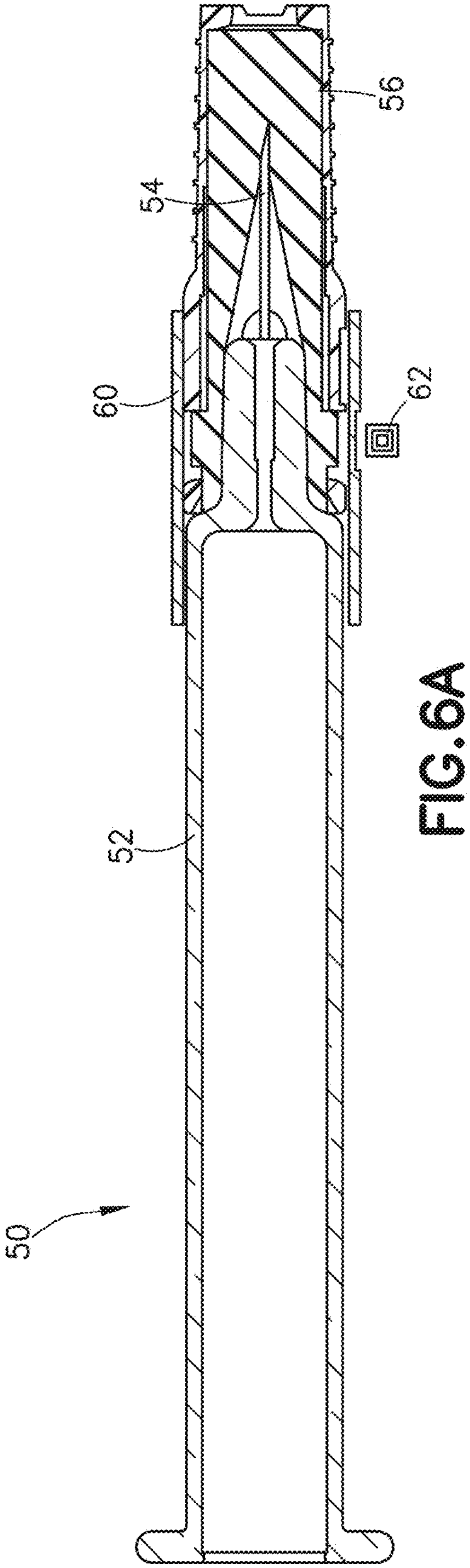
FIG. 6A is a cross-sectional side view of a syringe body and tip cap assembly incorporating a RFID label in accordance with an aspect of the present disclosure.
Figure 6B:
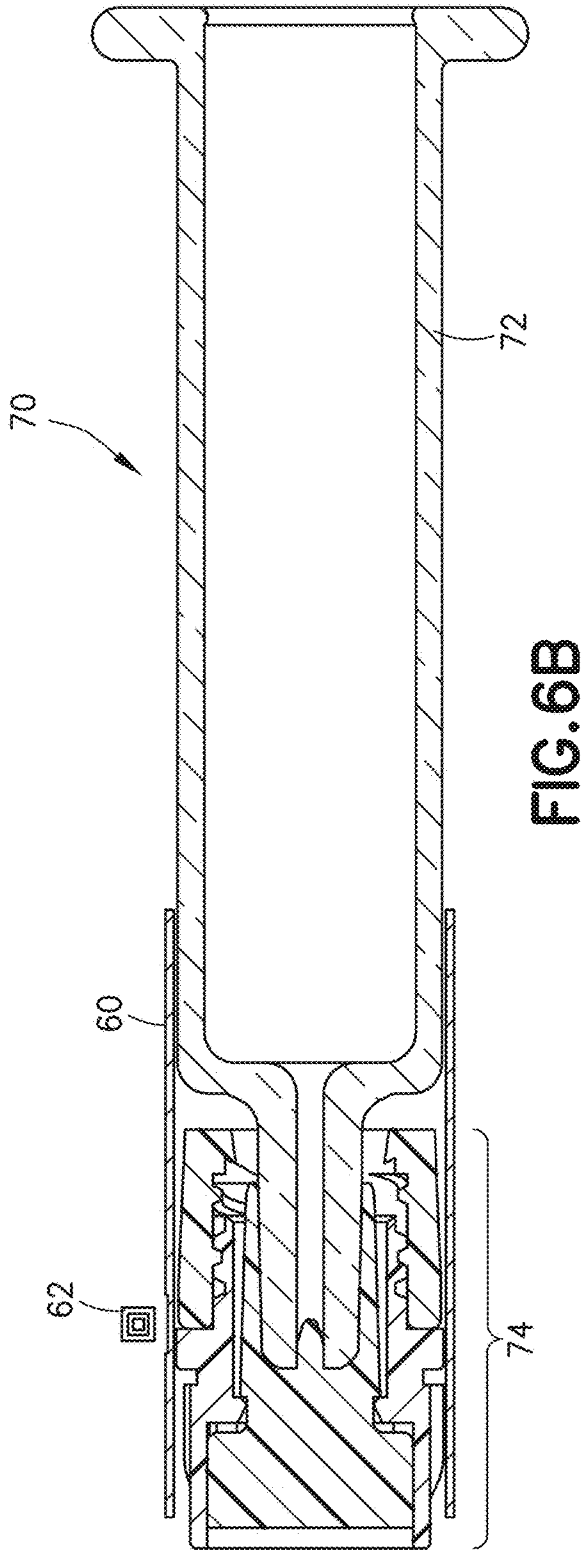
FIG. 6B is a cross-sectional side view of a syringe body and tip cap assembly in accordance with another aspect of the present disclosure.

Next, referring to FIGS. 6A and 6B, syringe and label configurations in accordance with another aspect of the present disclosure are shown.

Specifically, referring to FIG. 6A, a syringe and label assembly 50 is shown. Syringe and label assembly 50 includes a syringe body 52 having a needle 54 positioned at a distal end thereof, along with a tip cap 56 configured to be removably couplable to the syringe body 52 so as to selectively cover the needle 54. In the embodiment shown in FIG. 6A, the tip cap 56 is formed as a rigid needle shield (RNS) and a rubber inner shield and, thus, may simply be press-fit onto the tip portion of the syringe body 52. The rubber inner shield is at least partly inserted inside the rigid needle shield, which may be in nay plastic material known by the skilled person, and then the tip cap assembly is press fitted onto the tip portion of the syringe body 52.

Additionally, syringe and label assembly 50 may further include a label 60 having a RFID tag 62 integrated therein or thereon as, e.g., an inlay. In one embodiment, the label 60 is formed of a tubular, heat-shrinkable material. Accordingly, the label 60, in the form of a tube, may be inserted around the syringe body 52 such that the label 60 overlaps with both a distal portion of the syringe body 52 and a proximal portion of the tip cap 56. Then, heat (e.g., about 90° C.) may be applied to the label 60 so as to shrink the label 60 around a connection region of the syringe body 52 and the tip cap 56.

Alternatively, in another embodiment, the label 60 may be formed of a conventional label material (e.g., PET, PI, paper, etc.) and placed, via an adhesive, such that the label 60 overlaps with both a distal portion of the syringe body 52 and a proximal portion of the tip cap 56.

While not shown in FIG. 6A, the label 60 includes breakable bridges that open upon removal of the tip cap 56. Accordingly, the label 60 not only provides traceability via the RFID tag 62, but it also provides a visual indication to a user as to whether or not the tip cap 56 was removed from the syringe body 52. In this way, the label 60 provides a visual evidence of whether or not the medical device was tampered with or otherwise opened, enables traceability at the container lever (from syringe manufacture to syringe usage and disposal), and also helps to ensure that the tip cap 56 is not inadvertently removed from the syringe body 52.

Referring to FIG. 6B, a syringe and label assembly 70 is shown. Similar to syringe and label assembly 50 described above with respect to FIG. 6A, syringe and label assembly 70 utilizes the label 60, albeit in conjunction with a plastic rigid tip cap (PRTC) assembly 74 coupled to a syringe body 72, as opposed to an RNS tip cap. Thus, with the syringe and label assembly 70, the label 60 provides the same advantages as those described above (i.e., visual evidence of whether or not the medical device was tampered with or otherwise opened, enables traceability at the container lever (from syringe manufacture to syringe usage and disposal), etc.). Furthermore, the label 60 may also act to prevent unwanted rotation of the luer lock adaptor of the plastic rigid tip cap assembly 74, as well as in inadvertently removal of the plastic rigid tip cap assembly 74 from the syringe body 72.

Figure 7A:
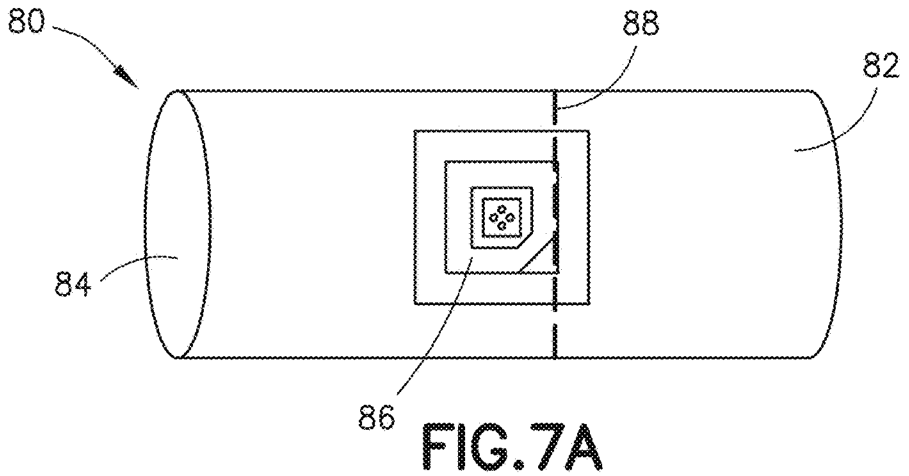
FIG. 7A is a side isometric view of tubular label incorporating a RFID tag in accordance with an aspect of the present disclosure.
Figure 7B:
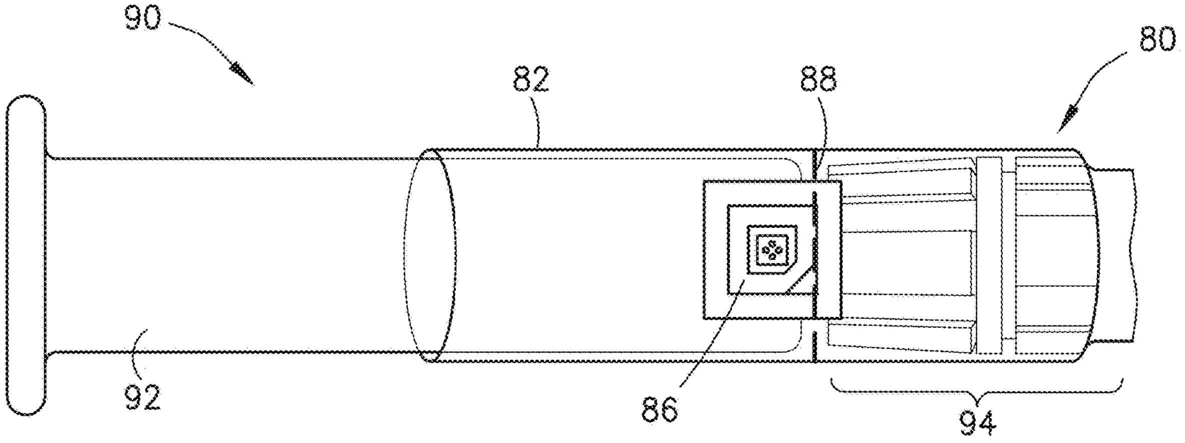
FIG. 7B is a side view of a syringe body and tip cap assembly incorporating the tubular label of FIG. 7A.
Figure 7C:
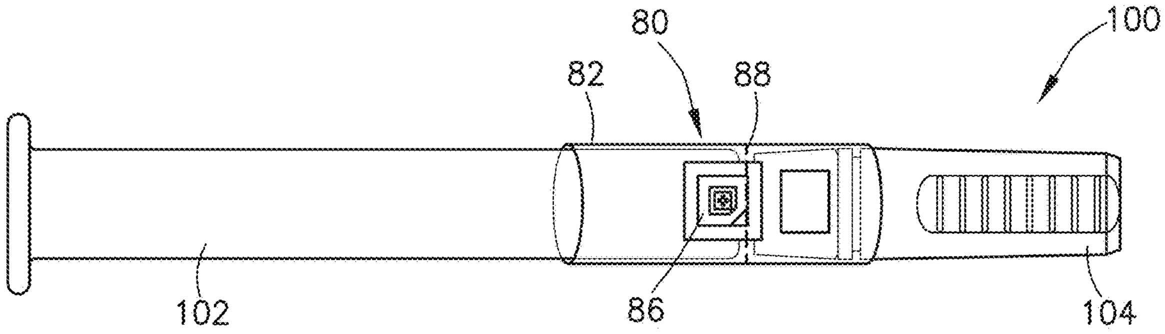
FIG. 7C is a side view of another syringe body and top cap assembly incorporating the tubular label of FIG. 7A.

Next, referring to FIGS. 7A-7C, syringe and label configurations in accordance with another aspect of the present disclosure are illustrated. Similar to label 60 described above, FIG. 7A shows a label 80 having a RFID tag 86 integrated therein or thereon as, e.g., an inlay. In one embodiment, the label 80 is formed of a tubular, heat-shrinkable material. Accordingly, referring to the syringe and label assembly 90 shown in FIG. 7B, the label 80, in the form of a tube 82, may be inserted around a syringe body 92 such that the label 80 overlaps with both a distal portion of the syringe body 92 and a proximal portion of a plastic rigid tip cap (PRTC) assembly 94 coupled to a syringe body 92. Then, heat (e.g., about 90° C.) may be applied to the label 80 so as to shrink the label 80 around a connection region of the syringe body 92 and the plastic rigid tip cap assembly 94.

FIG. 7C shows a similar syringe and label assembly 100 configuration, albeit pertaining to a syringe body 102 and a tip cap 104 (i.e., an RNS), wherein the tip cap 104 is configured to be removably couplable to the syringe body 102 so as to selectively cover a needle (not shown). The label 80 may be configured to slide over portions of the syringe body 102 and tip cap 104 around a connection region thereof.

Alternatively, in another embodiment, the label 80 may be formed of a conventional label material (e.g., PET, PI, paper, etc.), wherein the inner side 84 of the label 80 receives an adhesive (e.g. a rubber adhesive, an acrylic adhesive, etc.) such that the label 80 adheres to and overlaps with both a distal portion of the syringe body 92 and a proximal portion of the plastic rigid tip cap assembly 94 (in the case of syringe and label assembly 90 shown in FIG. 7B), or a distal portion of the syringe body 102 and a proximal portion of the tip cap 104 (in the case of syringe and label assembly 100 shown in FIG. 7C).

Referring still to FIGS. 7A-7C, label 80 further includes a tear-off etching line 88, which is a perforated line configured to allow for easier separation of the plastic rigid tip cap assembly 94 and the tip cap 104 from the syringe body 92 and the syringe body 102, respectively. Furthermore, as shown in FIGS. 7A-7C, tear-off etching line 88 is positioned along label 80 such that it passes through a portion of RFID tag 86. In this way, when the label 80 is broken along tear-off etching line 88, not only is a visual indication provided that the "seal" has been broken, but the machine-readable RFID signal provided by the RFID tag 86 is also altered. Thus, label 80 provides two forms of evidence in the event that the tip cap has been removed from the syringe (be it through tampering or authorized use).

As shown in FIGS. 7B and 7C, a majority of the RFID tag 86 on label 80 is provided on the syringe barrel side of the tear-off etching line 88. As such, even if the tip cap is removed from the syringe, the RFID tag 86 (and its unique identification data) remain attached to the syringe barrel, and can be provided on the same side as the drug label of the syringe. In this way, while tampering or other use of the syringe can be identified by way of RFID signal changes due to the label 80 being broken along tear-off etching line 88, the unique identification data associated with the syringe is not destroyed by this action.

Figure 8A:
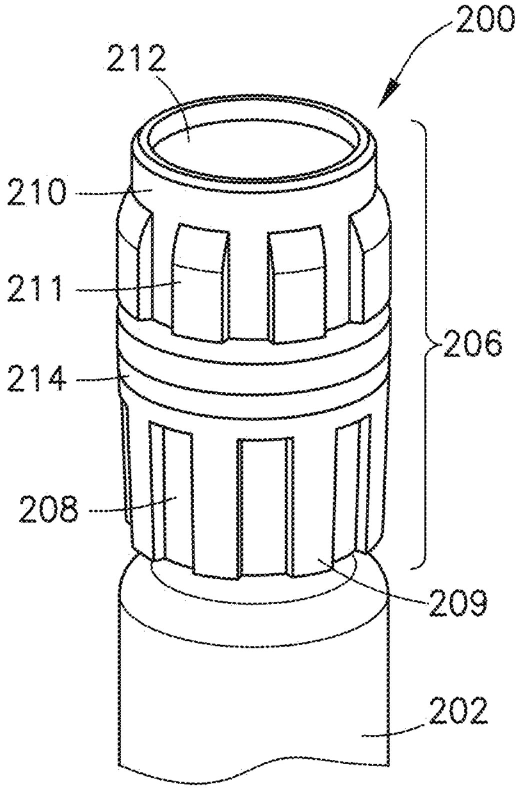
FIG. 8A is an isometric view of a syringe body and tip cap assembly incorporating a RFID tag in accordance with another aspect of the present disclosure.
Figure 8B:
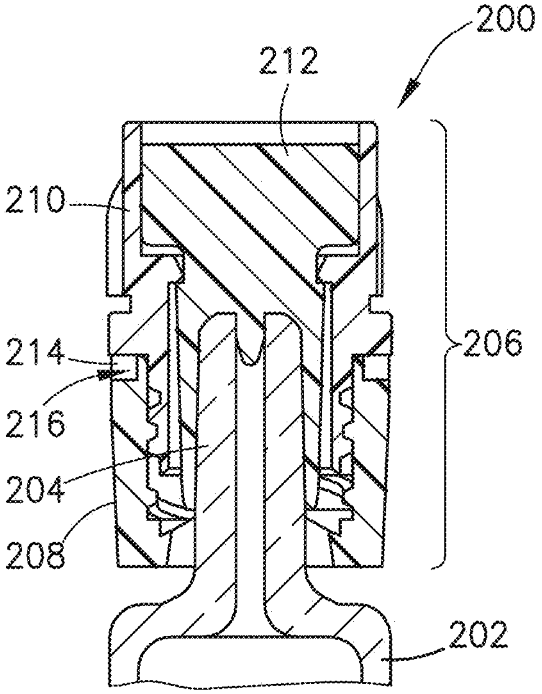
FIG. 8B is a cross-sectional side view of the syringe body and tip cap assembly incorporating a RFID tag of FIG. 8A.

Referring now to FIGS. 8A and 8B, a syringe body and tip cap assembly 200 in accordance with another aspect of the present disclosure is shown. The syringe body and tip cap assembly 200 includes a syringe body 202 having a tip portion 204, as well as a plastic rigid tip cap (PRTC) assembly 206. The plastic rigid tip cap assembly 206 is formed of multiple pieces, including a luer lock adaptor 208, a rigid cap 210, and a rigid tip cap 212 disposed within the rigid cap 210 and configured to at least partially surround the tip portion 204 of syringe body 202. As is shown in FIG. 8A, the luer lock adaptor 208 may include a plurality of ribs 209, while the rigid cap 210 may also include a plurality of ribs 211. The respective ribs 209, 211 may provide for enhanced grip by an assembly tool and/or a user's hand when attaching and/or removing the rigid cap 210, the luer lock adaptor 208, or both.

Additionally, at or near a parting line between the luer lock adaptor 208 and the rigid cap 210, a substantially ring-shaped RFID tag 214 may be provided. Specifically, as is shown in FIG. 8B, the RFID tag 214 may be inset within an annular groove 216 formed at a distal end of the luer lock adaptor 208. In this way, the formation of luer lock adaptor 208 via, e.g., molding is not substantially changed, but a secure, inset location upon the plastic rigid tip cap assembly 206 for the RFID tag 214 to reside is still provided. Furthermore, by placing the RFID tag 214 in the annular groove 216, the respective ribs 209, 211 remain unobscured, which is particularly advantageous when utilizing assembly tools to grasp the luer lock adaptor 208 and/or the rigid cap 211. While FIGS. 8A and 8B show the annular groove 216 being located at the distal end of the luer lock adaptor 208, it is to be understood that annular groove 216 may be located at any other location along the external surface of the luer lock adaptor 208, such as at the proximal end or proximal portion of the luer lock adaptor 208.

While not shown in FIGS. 8A and 8B, in another embodiment, it is to be understood that the rigid cap 210 may include a groove to house the RFID tag 214. Similarly, the groove need not be limited to placement at or near the parting line between the luer lock adaptor 208 and the rigid cap 210, and may be located anywhere along the plastic rigid tip cap assembly 206.

In some embodiments, RFID tag 214 may be over-molded onto the luer lock adaptor 208 at the location of groove 216. However, it is to be understood that the RFID tag 214 is not limited as such. For example, in some embodiments, the RFID tag 214 may be configured to be clipped onto the luer lock adaptor 208. Furthermore, while the RFID tag 214 is shown as being substantially ring-shaped, it is to be understood that the RFID tag 214 is not limited as such, and may be any appropriate shape capable of emitting a RFID signal.

The RFID tag 214 may formed as, e.g., an ultra-high frequency (UHF) RFID tag, a high frequency (HF) RFID tag, a high frequency-near-field communication (HF-NFC) RFID tag, and/or a low frequency (LF) RFID tag. Additionally and/or alternative, the antenna of RFID tag 214 may be a dipole, or may be made of one or several loops. Furthermore, while RFID tag 214 is shown and described herein, it is to be understood that other forms of remotely writable and readable data tags and/or inlays may be utilized in accordance with the present disclosure. For example, data tags or inlays such as Bluetooth tags, an ultra-wide-band real-time location system (RTLS), a WiFi RTLS, and/or an infrared RTLS may be utilized in lieu of (or in addition to) a RFID tag.

Figure 9A:
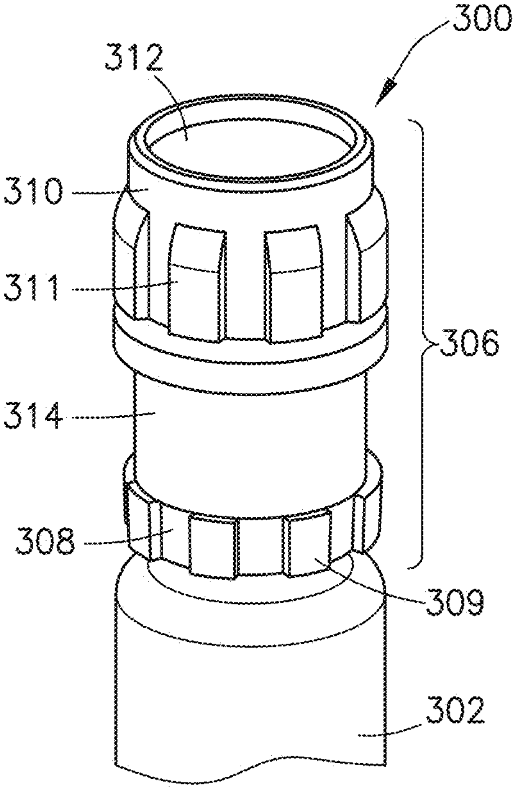
FIG. 9A is an isometric view of a syringe body and tip cap assembly incorporating a RFID tag in accordance with another aspect of the present disclosure.
Figure 9B:
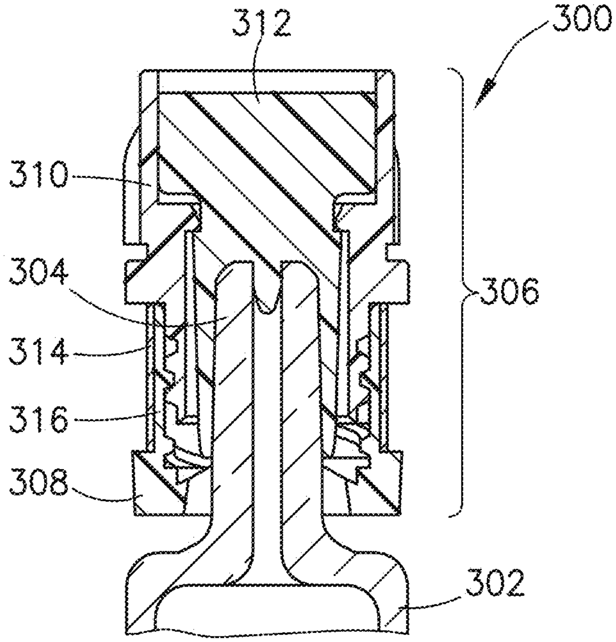
FIG. 9B is a cross-sectional side view of the syringe body and tip cap assembly incorporating a RFID tag of FIG. 9A.

Next, referring to FIGS. 9A and 9B, a syringe body and tip cap assembly 300 in accordance with another aspect of the present disclosure is shown. The syringe body and tip cap assembly 300 includes a syringe body 302 having a tip portion 304, as well as a plastic rigid tip cap (PRTC) assembly 306. The plastic rigid tip cap assembly 306 is formed of multiple pieces, including a luer lock adaptor 308, a rigid cap 310, and a rigid tip cap 312 disposed within the rigid cap 310 and configured to at least partially surround the tip portion 304 of syringe body 302. As is shown in FIG. 9A, the luer lock adaptor 308 may include a plurality of ribs 309, while the rigid cap 310 may also include a plurality of ribs 311. The respective ribs 309, 311 may provide for enhanced grip by an assembly tool and/or a user's hand when attaching and/or removing the rigid cap 310, the luer lock adaptor 308, or both.

As is shown in FIG. 9B, the luer lock adaptor 308 includes a distal portion 316, with ribs 309 not extending into the distal portion 316. In some embodiments, the distal portion 316 is inset. Substantially surrounding the distal portion 316 is a RFID tag 314. In this way, the formation of luer lock adaptor 308 via, e.g., molding is not substantially changed, but a secure, inset location for the RFID tag 314 to reside is still provided. Furthermore, by placing the RFID tag 314 at the distal portion 316 of luer lock adaptor 308, the respective ribs 309, 311 remain unobscured, which is particularly advantageous when utilizing assembly tools to grasp the luer lock adaptor 308 and/or the rigid cap 311.

In some embodiments, RFID tag 314 may be formed as an over-molded inlay so as to enable in-mold labeling onto the distal portion 316 of the luer lock adaptor 308. However, it is to be understood that the RFID tag 314 is not limited as such. The RFID tag 314 may formed as, e.g., an ultra-high frequency (UHF) RFID tag, a high frequency (HF) RFID tag, a high frequency-near-field communication (HF-NFC) RFID tag, and/or a low frequency (LF) RFID tag. Additionally and/or alternative, the antenna of RFID tag 314 may be a dipole, or may be made of one or several loops. Furthermore, while RFID tag 314 is shown and described herein, it is to be understood that other forms of remotely writable and readable data tags and/or inlays may be utilized in accordance with the present disclosure. For example, data tags or inlays such as Bluetooth tags, an ultra-wide-band real-time location system (RTLS), a WiFi RTLS, and/or an infrared RTLS may be utilized in lieu of (or in addition to) a RFID tag.

Figure 10A:
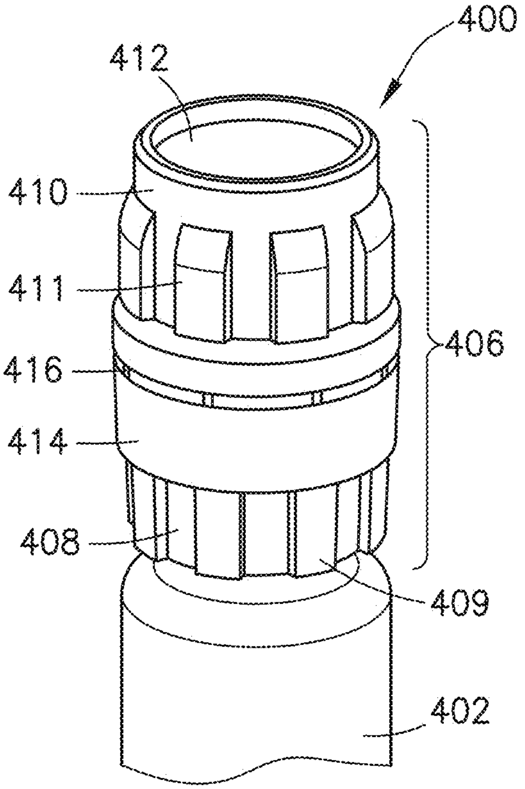
FIG. 10A is an isometric view of a syringe body and tip cap assembly incorporating a RFID tag in accordance with another aspect of the present disclosure.
Figure 10B:
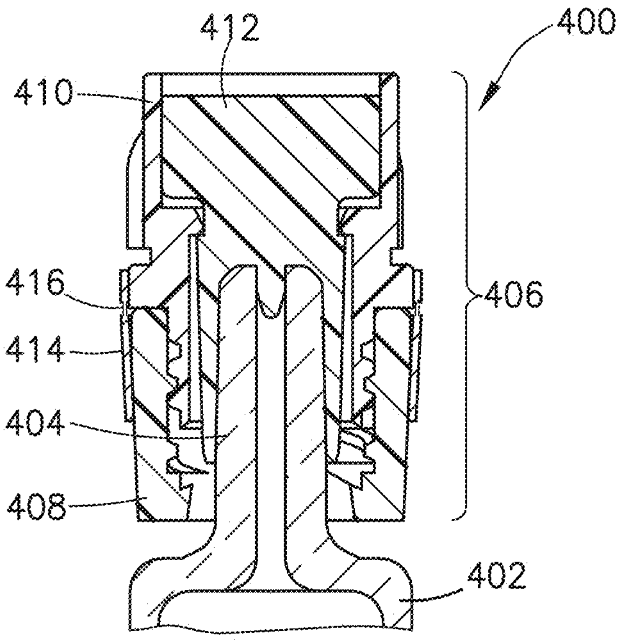
FIG. 10B is a cross-sectional side view of the syringe body and tip cap assembly incorporating a RFID tag of FIG. 10A.

Referring now to FIGS. 10A and 10B, a syringe body and tip cap assembly 400 in accordance with another aspect of the present disclosure is shown. Unlike the syringe body and tip cap assembly 300 described above with respect to FIGS. 9A and 9B, which utilizes a RFID tag 314 overlaying only the distal portion 316 of the luer lock adaptor 308, the syringe body and tip cap assembly 400 is configured to provide for evidence of tampering via relative rotation between the luer lock adaptor and rigid cap portions.

Specifically, the syringe body and tip cap assembly 400 includes a syringe body 402 having a tip portion 404, as well as a plastic rigid tip cap (PRTC) assembly 406. The plastic rigid tip cap assembly 406 is formed of multiple pieces, including a luer lock adaptor 408, a rigid cap 410, and a rigid tip cap 412 disposed within the rigid cap 410 and configured to at least partially surround the tip portion 404 of syringe body 402. As is shown in FIG. 10A, the luer lock adaptor 408 may include a plurality of ribs 409, while the rigid cap 410 may also include a plurality of ribs 411. The respective ribs 409, 411 may provide for enhanced grip by an assembly tool and/or a user's hand when attaching and/or removing the rigid cap 410, the luer lock adaptor 408, or both.

As is shown in both FIG. 10A and FIG. 10B, the syringe body and tip cap assembly 400 further includes a RFID tag 414 substantially surrounding both a distal portion of the luer lock adaptor 408 and a proximal portion of the rigid cap 410. In this way, the RFID tag 414 overlays the parting location of the luer lock adaptor 408 and a proximal portion of the rigid cap 410. At or near this parting location, the RFID tag 414 may further include a tear-off etching line 416. In this way, if and when the luer lock 408 and/or the rigid cap 410 are rotated relative to one another, the tear-off etching line 416 provides at least a visual indication that the "seal" has been broken, thereby providing effective evidence of tampering. Additionally and/or alternatively, if and when the tear-off etching line 416 is broken, the machine-readable RFID signal provided by the RFID tag 416 may also be altered or destroyed, thereby providing a machine-readable indication of tampering. Thus, in some embodiments, RFID tag 416 may provide two forms of evidence in the event that the elements of the plastic rigid tip cap (PRTC) assembly 406 have been separated (be it through tampering or authorized use).

As is shown in FIG. 10B, the RFID tag 414 substantially may surround both the distal portion of the luer lock adaptor 408 and the proximal portion of the rigid cap 410 in a way that does not require alteration of the luer lock adaptor 408 and/or the rigid cap 410 in order to accommodate the RFID tag 414. However, while not shown, it is to be understood that one or both of the luer lock adaptor 408 and the rigid cap 410 may be modified so as to improve the connection between the RFID tag 414 and the plastic rigid tip cap (PRTC) assembly 406.

Furthermore, by placing the RFID tag 414 at the distal portion of luer lock adaptor 408 and the proximal portion of the rigid cap 410, at least a portion of the respective ribs 409, 411 remain unobscured, which is particularly advantageous when utilizing assembly tools to grasp the luer lock adaptor 408 and/or the rigid cap 411.

In some embodiments, RFID tag 414 may be formed as a wet inlay so as to enable the RFID tag 414 to extend over portions of both the luer lock adaptor 408 and the rigid cap 411. However, it is to be understood that the RFID tag 414 is not limited as such. The RFID tag 414 may formed as, e.g., an ultra-high frequency (UHF) RFID tag, a high frequency (HF) RFID tag, a high frequency-near-field communication (HF-NFC) RFID tag, and/or a low frequency (LF) RFID tag. Additionally and/or alternative, the antenna of RFID tag 414 may be a dipole, or may be made of one or several loops. Furthermore, while RFID tag 414 is shown and described herein, it is to be understood that other forms of remotely writable and readable data tags and/or inlays may be utilized in accordance with the present disclosure. For example, data tags or inlays such as Bluetooth tags, an ultra-wide-band real-time location system (RTLS), a WiFi RTLS, and/or an infrared RTLS may be utilized in lieu of (or in addition to) a RFID tag.

While several embodiments of various syringe and label assemblies incorporating RFID tags are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A tip cap assembly for coupling with a syringe body, the tip cap assembly comprising:
- a tip cap configured to at least partially surround a tip portion of the syringe body;
- an RFID tag coupled to a distal end of the tip cap and oriented substantially transverse to a longitudinal axis of the tip cap; and
- a protective layer disposed distally over at least a portion of the RFID tag.

2. The tip cap assembly of claim 1, further comprising a cap, wherein the tip cap is disposed at least partially within the cap.

3. The tip cap assembly of claim 1, further comprising a luer lock adaptor coupled to the tip cap.

4. The tip cap assembly of claim 1, wherein the RFID tag is formed as a circular RFID inlay.

5. The tip cap assembly of claim 1, wherein the RFID tag extends across the entire distal end of the rigid tip cap.

6. The tip cap assembly of claim 1, wherein the RFID tag is one of an ultra-high frequency (UHF) RFID tag, a high frequency (HF) RFID tag, a high frequency-near-field communication (HF-NFC) RFID tag, or a low frequency (LF) RFID tag.

7. The tip cap assembly of claim 1, wherein the protective layer is one of a UV-cured adhesive, a rubber adhesive, or a silicon adhesive.

8. The tip cap assembly of claim 1, wherein the protective layer is a resin.

9. A syringe assembly, comprising:
- a syringe body having a tip portion;
- a tip cap configured to at least partially receive the tip portion therein;
- an RFID tag coupled to a distal end of the tip cap and oriented substantially transverse to a longitudinal axis of the syringe body; and
- a protective layer disposed distally over at least a portion of the RFID tag.

10. The syringe assembly of claim 9, further comprising a cap, wherein the tip cap is disposed at least partially within the cap.

11. The syringe assembly of claim 9, further comprising a luer lock adaptor coupled to the tip cap.

12. The syringe assembly of claim 9, wherein the RFID tag is formed as a circular RFID inlay.

13. The syringe assembly of claim 9, wherein the RFID tag extends across the entire distal end of the rigid tip cap.

14. The syringe assembly of claim 9, wherein the RFID tag is one of an ultra-high frequency (UHF) RFID tag, a high frequency (HF) RFID tag, a high frequency-near-field communication (HF-NFC) RFID tag, or a low frequency (LF) RFID tag.

15. The syringe assembly of claim 9, wherein the protective layer is one of a UV-cured adhesive, a rubber adhesive, a silicon adhesive, or a resin.

16. A method of manufacturing a tip cap assembly, comprising:
- providing a tip cap configured to at least partially surround a tip portion of a syringe body;
- positioning an RFID tag at a distal end of the tip cap and oriented substantially transverse to a longitudinal axis of the tip cap; and
- forming a protective layer disposed distally over at least a portion of the RFID tag.

17. The method of claim 16, further comprising:
- inserting at least a portion of the tip cap into a cap.

18. The method of claim 17, further comprising:
- coupling the cap to a luer lock adaptor.

19. The method of claim 16, wherein the RFID tag is formed as a circular RFID inlay.

20. The method of claim 16, wherein the protective layer is one of a UV-cured adhesive, a rubber adhesive, a silicon adhesive, or a resin.

* * * * *